United States Patent [19]
Sato

[11] Patent Number: 5,890,642
[45] Date of Patent: Apr. 6, 1999

[54] CLIP DRIVER

[76] Inventor: Hisao Sato, Fujimidai Mansion 2002, 29-10, Nukui 1-chome, Nerima-ku, Tokyo, Japan

[21] Appl. No.: 835

[22] Filed: Dec. 30, 1997

[51] Int. Cl.⁶ .................................................. A61B 17/00
[52] U.S. Cl. ........................ 227/134; 227/19; 227/120; 227/156; 29/243.56; 72/409.01; 72/409.04
[58] Field of Search ............................. 227/19, 120, 134, 227/156; 72/407, 409.01, 409.04; 29/243.56

[56] References Cited

U.S. PATENT DOCUMENTS

| | | | |
|---|---|---|---|
| 3,069,685 | 12/1962 | Anderau | 29/243.56 |
| 3,740,994 | 6/1973 | DeCarlo, Jr. | 227/19 |
| 3,780,416 | 12/1973 | Rider | 29/243.56 |
| 3,889,338 | 6/1975 | Hosaka | 72/409.01 |
| 4,408,603 | 10/1983 | Blake, III et al. | 227/DIG. 1 |
| 5,136,768 | 8/1992 | Sato | 227/156 |
| 5,152,423 | 10/1992 | Tseng | 29/243.56 |
| 5,619,789 | 4/1997 | Chung | 29/243.56 |

*Primary Examiner*—Scott A. Smith
*Attorney, Agent, or Firm*—Kanesaka & Takeuchi

[57] ABSTRACT

A clip driver for driving clips each having a back portion, and abutment portions so that the frontmost clip can hold sheets of paper between the opposite ends of the abutment portions, comprising: a driver body for accommodating a plurality of the clips, the driver body including a paper insertion inlet formed at a front end for inserting the sheet-like members to be clipped, a clip insertion hole formed at a rear end for inserting the clips one by one, and a clip path formed to extend from the paper insertion inlet to the clip insertion inlet; a pair of clip opening springs disposed on the driver body near the paper insertion inlet for opening a nip between the abutment portions of the clip in the opposite directions; a slide is disposed in the driver body on the front end side so as to be movable in a front/rear direction for feeding a frontmost one of the clips in the clip path toward the paper insertion inlet over the clip opening springs by a front end of the slide; a handle one end of which is pivotally supported on the rear end side of the driver body rotatably and movably in the front/rear direction while the other end of which is disposed on the front end side of the driver body; and a connection mechanism for connecting the driver body, the slide and the handle to each other so as to move the slide in the front/rear direction in response to the rotation and movement of the handle means.

10 Claims, 11 Drawing Sheets

CLIP DRIVER

BACKGROUND OF THE INVENTION

1. Field of the Invention

The present invention relates to a clip driver for clipping sheets of paper of documents or the like, and particularly relates to a clip driver capable of storing a plurality of clips each of which is formed by bending an elastic plate-like body so as to have abutment portions on its longitudinally opposite ends, so that the clips are sequentially fed to a clip opening position in which the abutment portions of each clip are opened so as to hold the sheets of paper between the abutment portions.

2. Description of the Related Art

In JP-Y-58-4698, the Applicant of this application has proposed not only a clip which is formed of a sheet of elastic plate-like member so as to have a back portion formed at the longitudinal center of the plate-like member and abutment portions formed so as to be continued to this back portion so that their front ends abut against each other, but also a clip driver for opening the abutment portions of such a clip so as to make the clip hold sheets of paper such as documents between the abutment portions. This clip driver is constituted by: a driver body having an insertion inlet formed at its front end for inserting end portions of sheets of paper to be clipped, a clip insertion inlet formed at its rear end, and a storage portion formed in its inside for storing clips; an clip opening spring provided near the insertion inlet in the driver body so as to be inserted between the abutment portions of a clip to thereby open the abutment portions against the elasticity of the clip; and a lever storably inserted into the storage portion from the rear end of the storage portion so as to engage with a back portion of a clip to thereby push the clip toward the insertion opening. When sheets of paper are to be clipped, the sheets of paper are inserted to the insertion inlet, and a clip is moved toward the insertion inlet by the lever. As the clip is further moved, the clip opening spring is inserted into the opening between the abutment portions of the clip. The clip is further moved toward the insertion inlet while opening the abutment portions to reach a position where the sheets of paper placed in the insertion inlet are sandwiched between the abutment portions of the clip. When the lever is moved further forward, the clip is removed from the clip opening spring, so that the clip is ejected from the insertion inlet in a state where the clip holds the sheets of paper between the abutment portions.

In the clip driver proposed in the above-mentioned JP-Y-58-4698, there was a defect that it was impossible to charge a plurality of clips in the storage portion because one clip is pushed out by the front end of the lever. Therefore, in U.S. Pat. No. 4,353,157, the inventor of this application proposed a clip driver in which a knob was provided on the upper surface of a storage portion of a driver body so that the knob could slide in the front/rear direction and the front end portion of the knob could move down. In the clip driver, by advancing this knob while pushing down it, a clip was pushed out to the position of an clip opening spring. At the same time, a plurality of clips could be charged in a storage portion. After the first clip was pushed out, the knob was moved back to abut against the back portion of the next clip, so that the next clip could be moved to the portion of the clip opening springs. In this clip driver proposed in U.S. Pat. No. 4,353,157, it was necessary to move back the knob whenever a new clip was to be positioned to the portion of the clip opening springs, so that there was a problem that the operation was troublesome, although a plurality of clips could be stored so that a plurality of sets of sheets of paper could be clipped continuously.

Therefore, in U.S. Pat. No. 4,996,755, the inventor of this application further proposed a clip driver in which a knob protrusion projected over the upper surface of the front end of a knob, while the knob was always kept backward and upward by a spring. When sheets of paper were to be clipped by this clip driver, the knob was pushed down against the elastic force of the spring and moved forward to thereby push out a first clip. Since the knob was moved up and back when the thumb handling the knob was separated from the knob, the knob could move back without being disturbed by the next clip to push out the next clip.

According to the clip driver in U.S. Pat. No. 4,996,755, it is possible to clip end portions of sheets of paper only by the operation to move the knob forward, and it is possible to clip sets of sheets of paper continuously. However, it is necessary to operate the knob only by a thumb, so that there is a problem that some manual dexterity is required for the operation to move the knob forward while pushing it down.

SUMMARY OF THE INVENTION

It is therefore an object of the present invention to solve the foregoing problems.

It is another object of the present invention to provide a clip driver by which clipping can be performed with an easy operation of simple manual gripping.

In order to achieve the above objects, according to a first aspect of the present invention, provided is a clip driver for driving clips each of which is formed from an elastic plate-like body so as to be constituted by a back portion, and abutment portions formed by bending the elastic plate-like body in the same direction at opposite ends of the back portion so that opposite ends of the abutment portions abut against each other elastically whereby the clip can hold edge portions of sheet-like members to be clipped between the opposite ends of the abutment portions, comprising: a driver body for accommodating a plurality of the clips, the driver body including a paper insertion inlet formed at a front end for inserting the sheet-like members to be clipped, a clip insertion hole formed at a rear end for inserting the clips one by one, and a clip path formed to extend from the paper insertion inlet to the clip insertion inlet; a pair of clip opening springs disposed on the driver body near the paper insertion inlet for opening a nip between the abutment portions of the clip in the opposite directions; a slide means disposed in the driver body on the front end side so as to be movable in a front/rear direction for feeding the frontmost one of the clips in the clip path toward the paper insertion inlet over the clip opening springs by means of a front end of the slide means; a handle means one end of which is pivotally supported on the rear end side of the driver body rotatably and movably in the front/rear direction while the other end of which is disposed on the front end side of the driver body; and a connection means for connecting the driver body, the slide means and the handle means to each other so as to move the slide means in the front/rear direction in response to the rotation and movement of the handle means to thereby feed the clip to the paper insertion inlet over the clip opening springs.

According to a second aspect of the present invention, in the clip driver according to the first aspect, a front-end upper portion of the clip path in the driver body is open to form an opening, and the slide means is disposed movably in the front/rear direction so as to close the opening partially.

According to a third aspect of the present invention, in the clip driver according to the first aspect, the slide means has an elastic member for enabling the slide means to move forward when one end of the handle means moves forward while rotating, and for making the slide means move backward by an elastic force of the elastic member when the handle means returns.

According to a fourth aspect of the present invention, in the clip driver according to the first aspect, the driver body has a pair of side wall portions provided so as to stand at a distance in a direction perpendicular to the front/rear direction, and a support shaft provided across the side wall portions perpendicularly thereto on the rear end side of the driver body; and the handle means includes a handle body having long holes formed in a rear end portion of the handle body so as to extend in the front/rear direction so that the support shaft is inserted rotatably in the long hole.

According to a fifth aspect of the present invention, in the clip driver according to the first aspect, the connection means has a first connection member one end of which is connected to the driver body and the other end of which is connected to the handle means rotatably, and a second connection member one end of which is connected to the handle means and the other end of which is connected to the slide means rotatably, the first and second connection members moving the handle means and the slide means in the front/rear direction respectively by pressing the handle means.

According to a sixth aspect of the present invention, in the clip driver according to the fifth aspect, the first connection means is constituted by a pair of link bars disposed to sandwich opposite sides of the driver body, while the second connection member is constituted by a single link bar disposed to rotate between the opposite sides of the driver body.

According to a seventh aspect of the present invention, in the clip driver according to the first aspect, the driver body includes a pair of side wall portions provided to stand at a distance in a direction perpendicular to the front/rear direction of the driver body, and a support shaft provided across the side wall portions so as to extend perpendicularly to the side wall portions on the rear end side of the driver body; the handle means includes a handle body having a long hole extending in the front/rear direction so that the support shaft is inserted rotatably in the long hole at a rear end portion of the handle body; the connection means has a first connection member one end of which is connected to the driver body and the other end of which is connected to the handle means rotatably, and a second connection member one end of which is connected to the handle means and the other end of which is connected to the slide means rotatably; and the slide means has an elastic member one end of which is connected to the support shaft and the other end of which is connected to the slide means for enabling the slide means to move forward when one end of the handle means moves forward while rotating, and for making the slide means move backward by an elastic force of the elastic member when the handle means returns.

According to an eighth aspect of the present invention, in the clip driver according to the first aspect, the handle means includes a handle body one end of which is pivotally supported on the rear end side of the driver body so as to be rotatable and movable in the front/rear direction, a handle cover which is formed to cover the handle body and at least an upper surface of which is transparent to be able to see an upper surface of the handle body through the upper surface of the handle cover.

According to a ninth aspect of the present invention, in the clip driver according to the first aspect, a print medium on which a company name, a trade name, an official notice, etc. are printed is put on the upper surface of the handle body.

According to a tenth aspect of the present invention, in the clip driver according to the first aspect, a lower space is provided in a bottom portion on the rear end side of the driver body, the lower space accommodating a stand lever for positioning the driver body obliquely so that the paper insertion inlet side is put down while the clip insertion inlet side is put up when the stand lever is set up.

DETAILED DESCRIPTION OF THE PREFERRED EMBODIMENT

Figure 15:
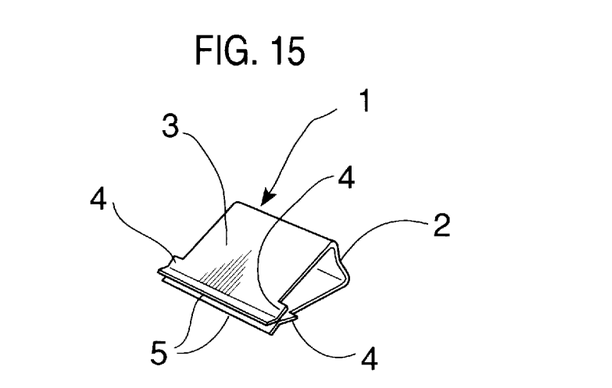
FIG. 15 is a perspective view illustrating an example of a clip used in the embodiment.

A clip driver of an embodiment according to the present invention will be described below with reference to the accompanying drawings. First, an example of well-known clip used in this clip driver will be described with reference to FIG. 15 which is a perspective view illustrating such a clip. A clip 1 is formed by bending an approximately rectangular plate-like body consisting of a metal plate or a synthetic plate. The clip 1 is constituted by: a back portion 2 which is formed at the longitudinally center of the plate-like body so as to have a length substantially corresponding to the maximum clipping thickness and so as to be curved inward; a pair of abutment portions 3 formed by bending the plate-like body at the longitudinally opposite end portions of the back portion 2 in the same direction so that the opposite end portions of the abutment portions can abut against each other elastically; and lug portions 4 provided on the edge portions of the respective abutment portions 3 so as to project in the width direction, that is, the direction perpendicular to the longitudinal direction, respectively. In the free ends of the respective abutment portions 3 including these lug portions 4, guide portions 5 bent outward respectively are formed so as to be opened easily.

Figure 1:
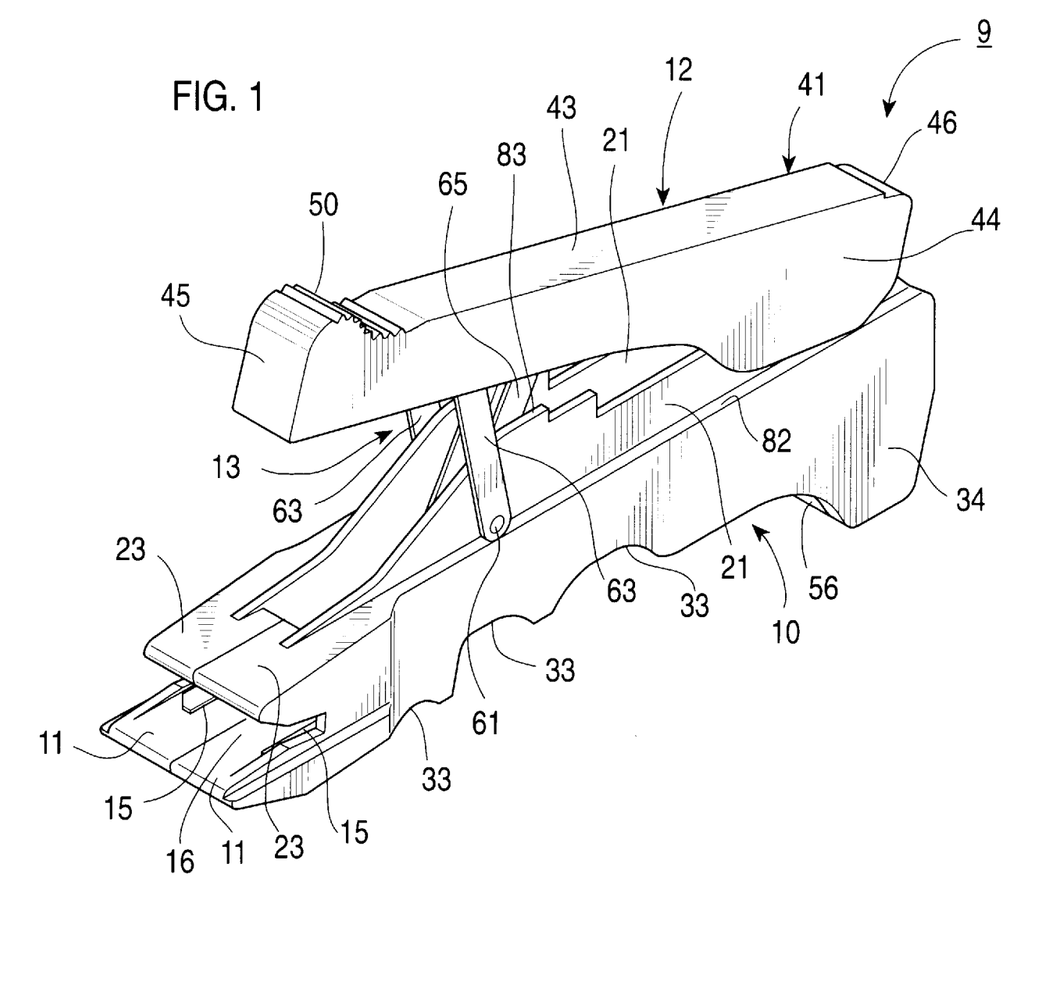
FIG. 1 is a perspective view illustrating an embodiment of the present invention.
Figure 2:
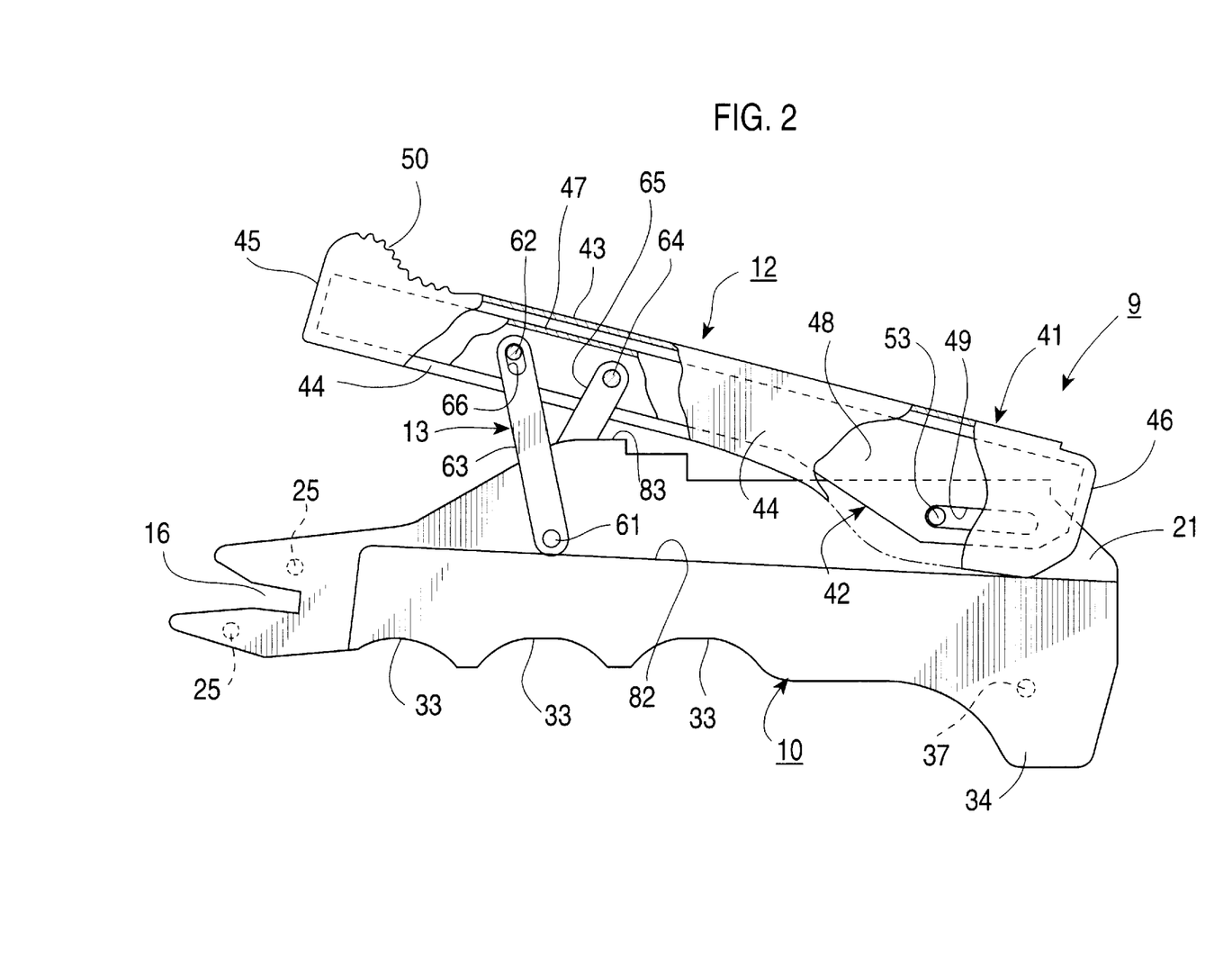
FIG. 2 is a partially cutaway side view illustrating the embodiment.
Figure 3:
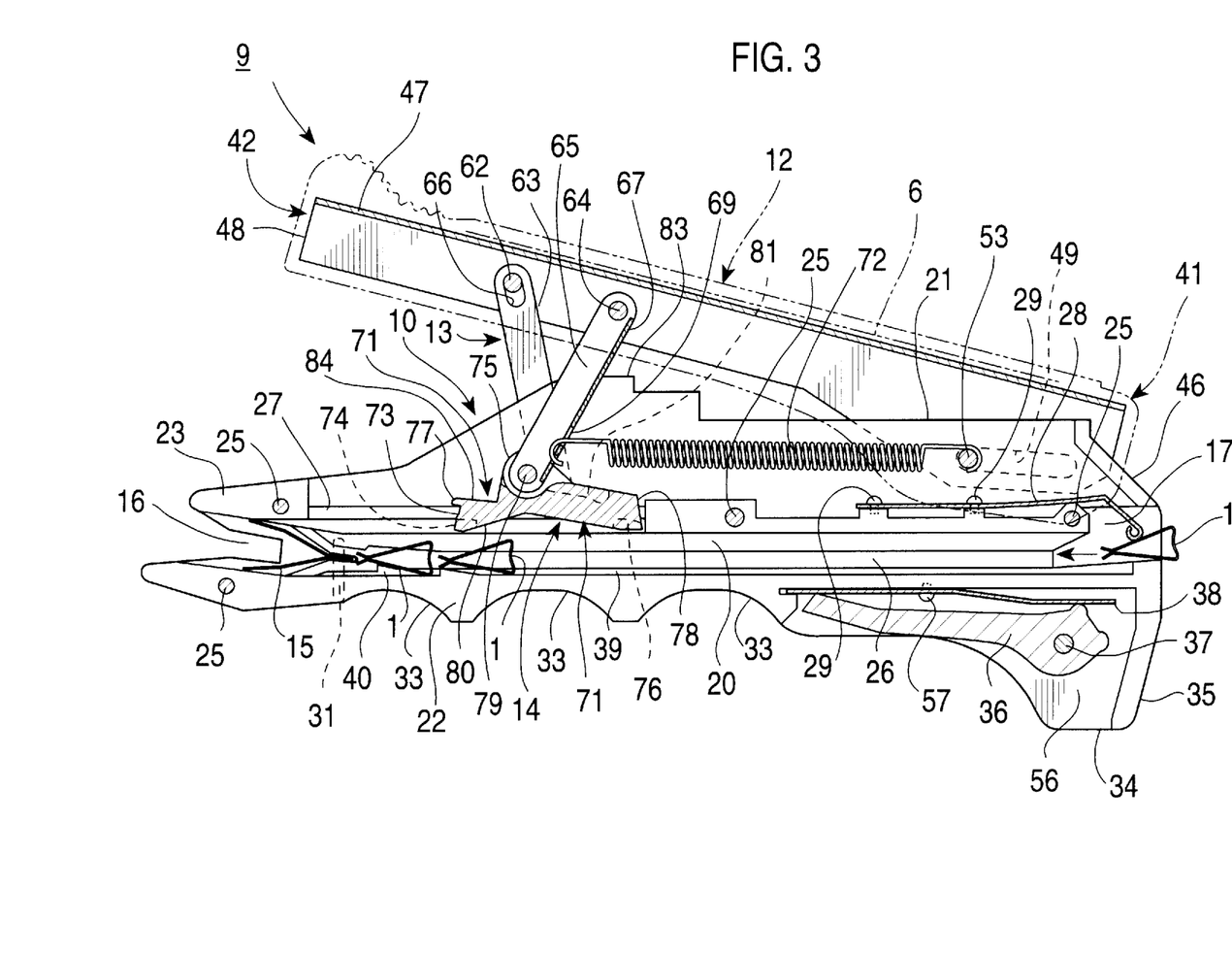
FIG. 3 is a vertically sectioned side view illustrating the embodiment with clips.
Figure 4:
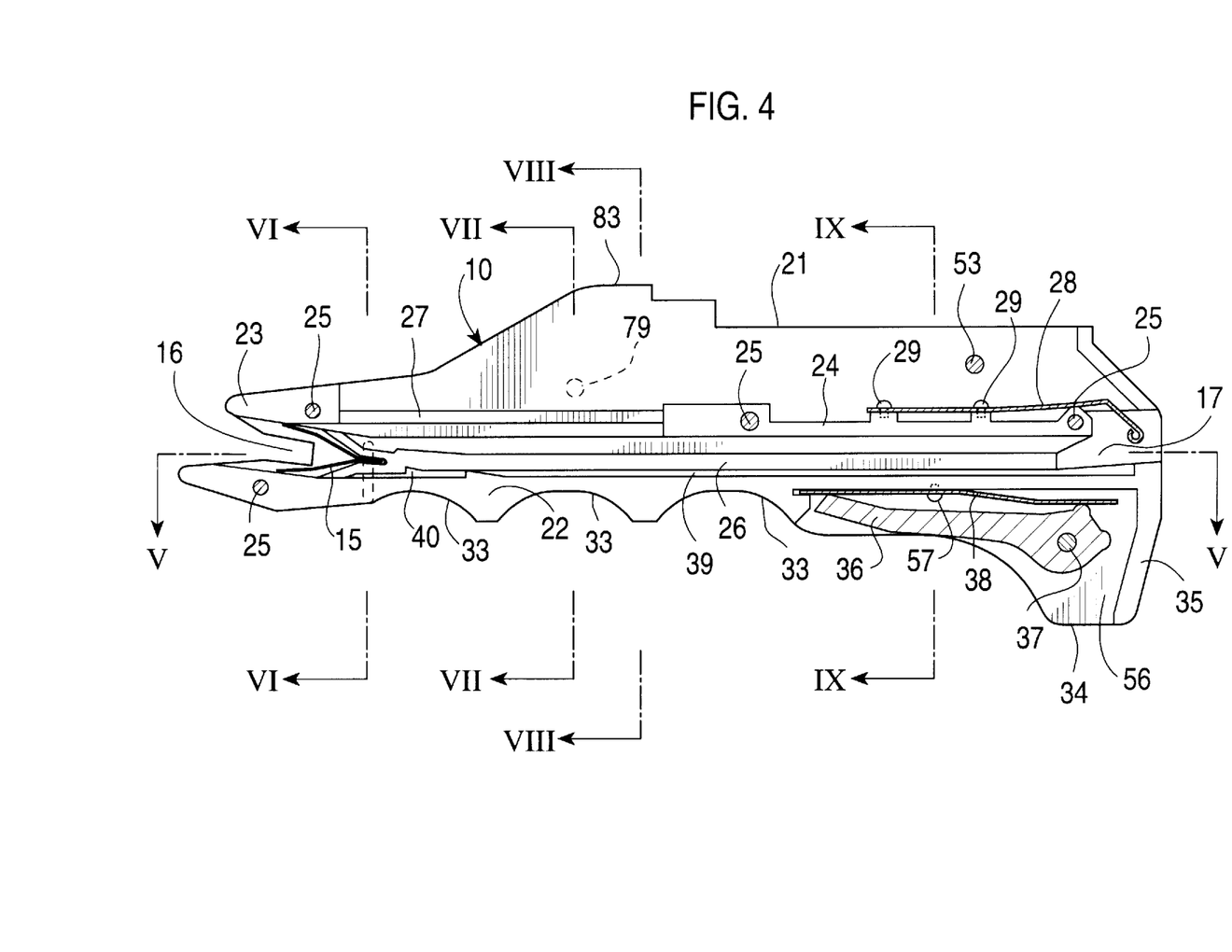
FIG. 4 is a vertically sectioned side view illustrating only a body portion in the embodiment.
Figure 5:
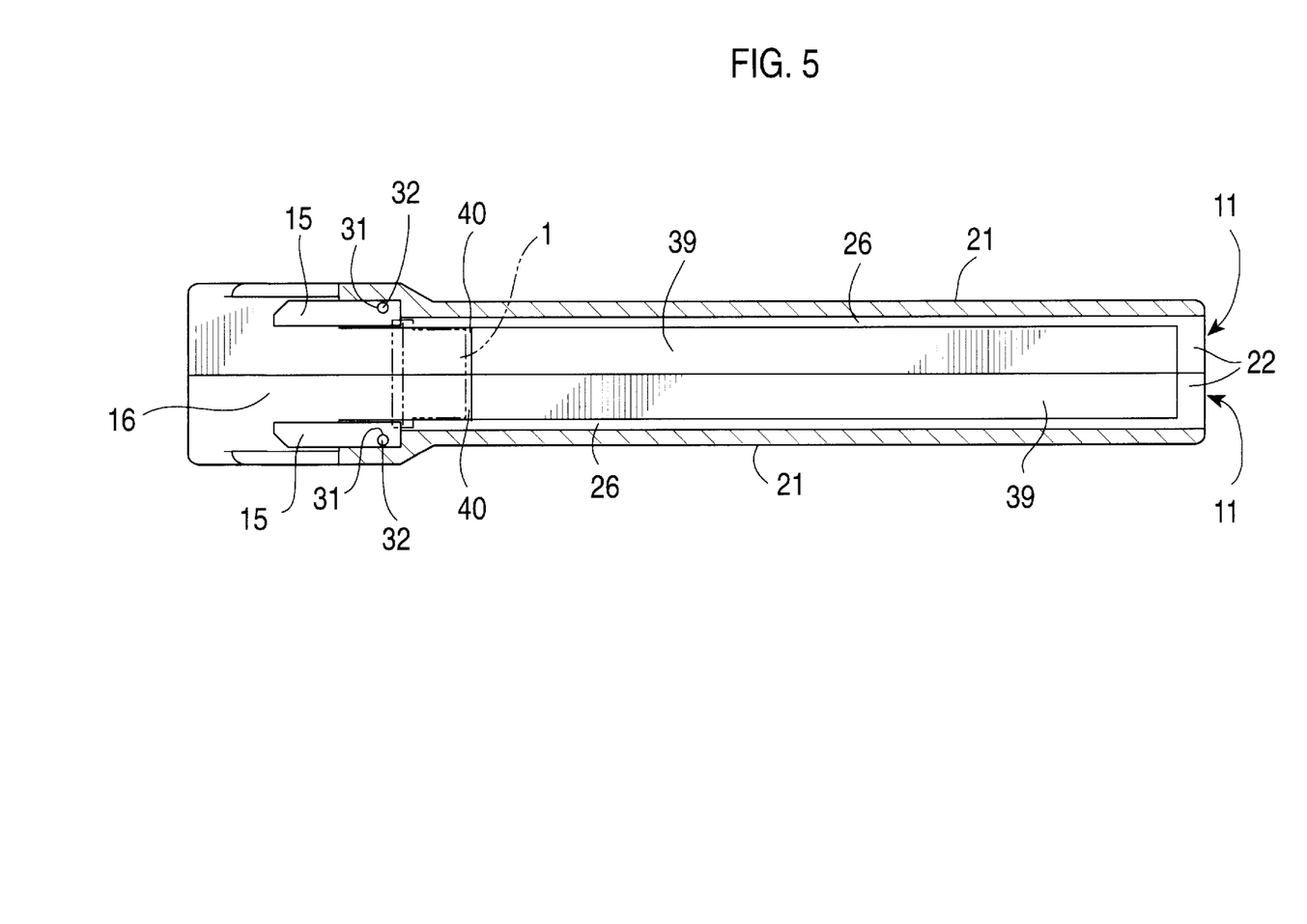
FIG. 5 is a horizontally sectioned view taken on line V—V of FIG. 4.
Figure 6:
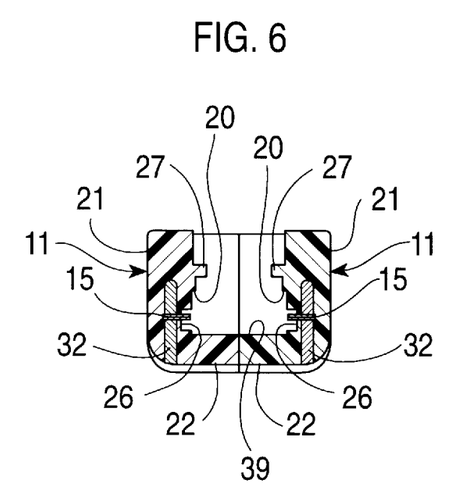
FIG. 6 is a cross-sectional view taken on line VI—VI of FIG. 4.
Figure 7:
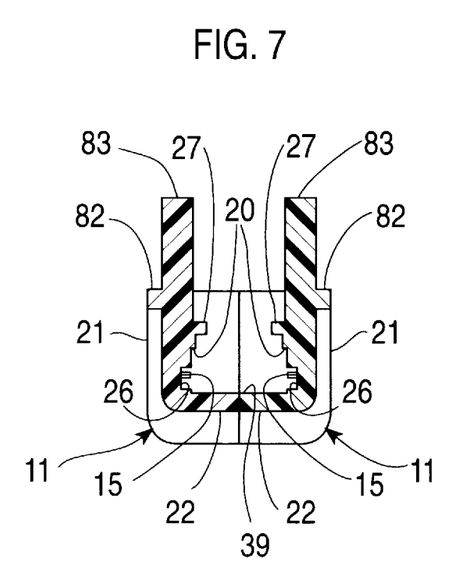
FIG. 7 is a cross-sectional view taken on line VII—VII of FIG. 4.
Figure 8:
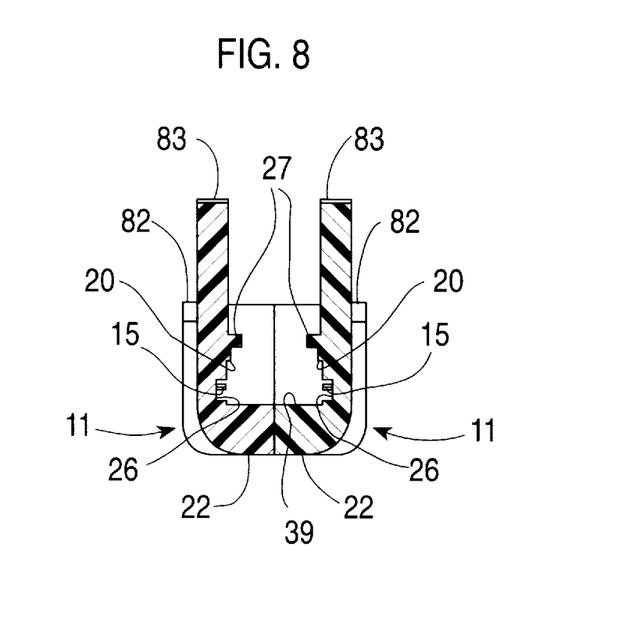
FIG. 8 is a cross-sectional view taken on line VIII—VIII of FIG. 4.
Figure 9:
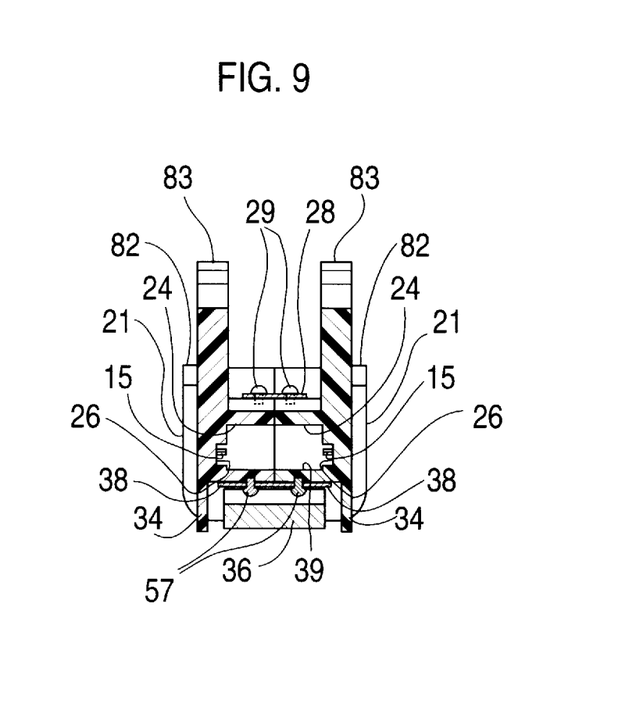
FIG. 9 is a cross-sectional view taken on line IX—IX of FIG. 4.
Figure 10:
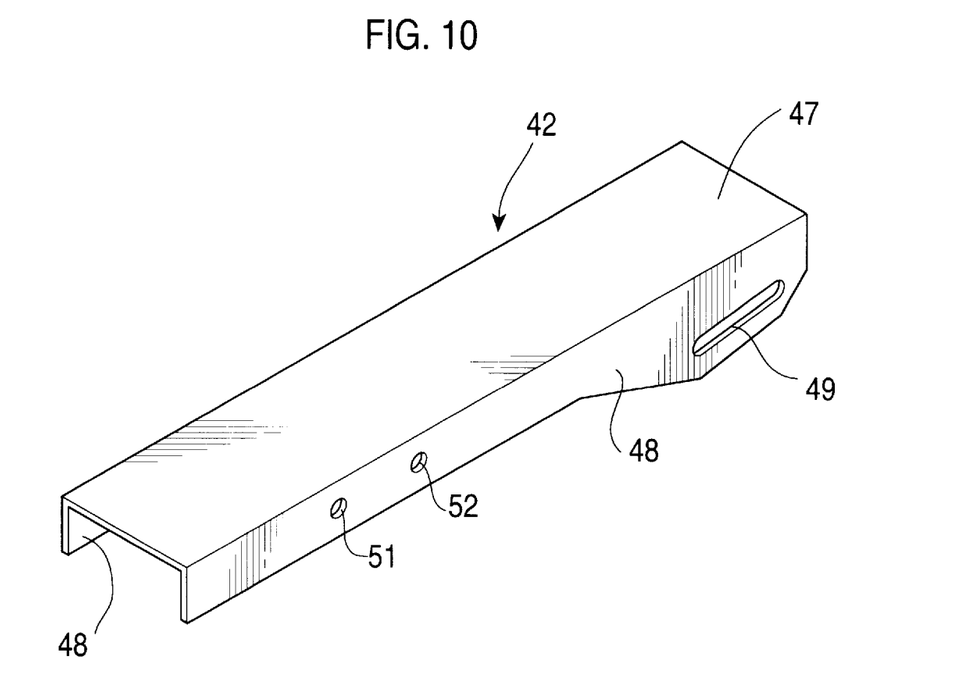
FIG. 10 is a perspective view illustrating only a handle body in the embodiment.
Figure 11:
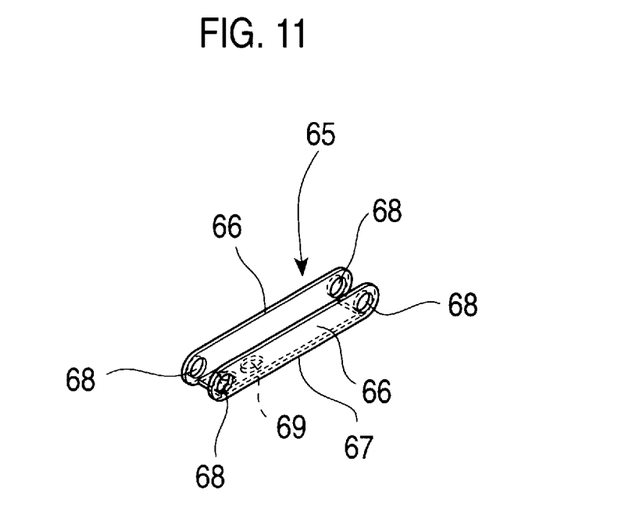
FIG. 11 is a perspective view illustrating only a second lever member in the embodiment.

Next, a clip driver for clipping sheets of paper with such a clip 1 will be described with reference to FIGS. 1 to 11. FIG. 1 is a perspective view illustrating an embodiment of the present invention; FIG. 2 is a partially cutaway side view illustrating the embodiment; FIG. 3 is a vertical sectional side view illustrating the embodiment with clips; FIG. 4 is a vertical sectional side view illustrating only a driver body portion in the embodiment; FIG. 5 is a cross-sectional view taken on line V—V of FIG. 4; FIG. 6 is a cross-sectional view taken on line VI—VI of FIG. 4; FIG. 7 is a cross-sectional view taken on line VII—VII of FIG. 4; FIG. 8 is a cross-sectional view taken on line VIII—VIII of FIG. 4; FIG. 9 is a cross-sectional view taken on line IX—IX of FIG. 4; FIG. 10 is a perspective view illustrating only a handle body in the embodiment; and FIG. 11 is a perspective view illustrating only a second lever member in the embodiment.

A clip driver 9 is constituted mainly by a driver body 10 longitudinally divided into a pair of driver body portions 11, a handle portion 12 attached on the driver body 10 so as to cover the upper portion of these driver body portions 11, a link portion 13 supporting the front end portion of the handle portion 12 on the driver body 10 so that the front end portion of the handle portion 12 can move down forward, a slide member 14 for feeding the clip 1 toward a paper sheet clipping position by means of this link portion 13, and a pair of clip opening springs 15 for opening the abutment portions 3 of the clip 1. A paper insertion inlet 16 to which edge portions of sheets of paper to be clipped are to be inserted is formed at one end of the driver body 10, while a clip insertion inlet 17 for charging the clip 1 is formed at the other end. In the following description, "front" or "front end" means the side or end at the paper insertion inlet 16 side, while "rear" or "rear end" means the side or end at the clip insertion inlet 17 side. In addition, "moving forward" means moving toward the paper insertion inlet 16, while "moving backward" means moving toward the clip insertion inlet 17.

The pair of driver body portions 11 formed from synthetic resin, and have the same structure with each other. Therefore, the structure of one of the driver body portions 11 will be described below in detail by way of example. As shown in FIGS. 1 and 4 to 9, the driver body portion 11 has a side portion 21, a bottom portion 22, a front end upper cover portion 23 covering the front end upper portion of the side portion 21 and constituting a part of the paper insertion inlet 16 together with the bottom portion 22 disposed under the side portion 21, and a ceiling portion 24 provided at the rear of the side portion 21 and disposed at a predetermined distance from the upper surface of the bottom portion 22 disposed under the side portion 21. The respective free ends of the bottom portion 22, the front end upper cover portion 23 and the ceiling portion 24 of one of the driver body portions 11 are brought into contact with the respective free ends of the bottom portion 22, the front end upper cover portion 23 and the ceiling portion 24 of the other driver body portion 11. After that, screws 25 are inserted from four holes formed in one of the driver body portions 11 and screwed into four corresponding screw holes formed in the other driver body portion 11. Accordingly, there is provided a case the upper side of which is opened in a region from the rear end of the front end upper cover portion 23 to the front end of the ceiling portion 24, and in which a hollow portion is formed to store a plurality of clips 1 therein. Although the case is vertically divided into two in the longitudinal direction in this embodiment, it is not limited to this, but, for example, it may be cut horizontally in the longitudinal direction into a plurality of portions.

In the inner surface of the side portions 21 of the driver body portion 11, a clip guide groove 20 with which the abutment portion 3 of the clip 1 movably engages is formed slightly above the upper surface of the bottom portion 22 so as to extend from the paper insertion inlet 16 to the clip insertion portion 17. A lug guide groove 26 in which the lug portion 4 of the clip 1 movably engages is further formed in the clip guide groove 20. Above this lug guide groove 26 and in the open portion between the rear end of the front end upper cover portion 23 and the front end of the ceiling portion 24, a protrusion 27 is formed so as to project substantially perpendicularly to the inner surface of the side portion 21. A belt-like insertion inlet cover 28 narrower in width than the ceiling portion 24 is mounted at its one end on the upper surface of the ceiling portion 24. The insertion inlet cover 28 is constituted, for example, by a metal plate having spring characteristic. One end of the insertion inlet cover 28 is fixed to the upper surface of the ceiling portion 24 by a stop pin 29 while its other end is a free end. The free end of the insertion inlet cover 28 covers the clip insertion inlet 17 elastically except a slight open portion, so that the clip 1 does not come off from the clip insertion inlet 17. When the clip 1 is inserted to the clip insertion inlet 17, the guide portions 5 of the clip 1 may be inserted into the open portion of the clip insertion inlet 17 which is not covered with the edge of the insertion inlet cover 28, and further inserted while pushing up the edge of the insertion inlet cover 28 by the slopes of the abutment portions 3, as shown in FIG. 3.

The clip opening springs 15 are attached to the paper insertion inlet 16 side end portions of the lug guide grooves 26 of the driver body 10. When the clip 1 reaches these end portions, the clip opening springs 15 are inserted between the lug portions 4 through the guide portions 5 of the clip 1, so that the abutment portions 3 are opened at the lug portions 4. Each of the clip opening springs 15 is formed into an approximately toppled V-shape in vertical section, so that the apex of the V-shape is disposed on the clip insertion inlet 17 side while the opened free ends of the V-shape is disposed on the paper insertion inlet 16 side. The clip opening springs 15 are fixed to the inner sides of the side portions of the driver body portions 11 by stop pins 32 inserted from the bottom portion 22 of the driver body portions 11 into insertion holes 31 (see FIG. 5) formed in the apexes of the clip opening springs 15. These insertion holes 31 and stop pins 32 are formed in the positions not to prevent the lug portions 4 of the clip 1 from passing the clip opening springs 15.

Three recess portions 33 on which first to third fingers can be placed are formed in the lower surface on the front end side in the bottom portion 22 of each of the driver body portions 11. On the rear end side of the bottom portion 22, a lower side portion cover 34 and a lower rear portion cover 35 are formed to cover the side surface and rear end portions of the bottom portion 22. A stand lever 36 is stored in a lower space 56 surrounded by the lower side portion covers 34 and the lower rear portion cover 35. If this stand lever 36 is set up, the clip driver 9 can be put slantingly in a manner so that the paper insertion inlet 16 side is put down while the clip insertion inlet 17 side is put up when the clip driver 9 is used on a desk or the like. Pin-like protrusions 37 are formed on one-end side surfaces of the opposite sides of the stand lever 36 so as to outward project substantially perpendicularly to the opposite sides of the stand lever 36. The pin-like protrusions 37 are fitted into shaft holes (not shown) made in the inner surfaces of the lower side portion covers 34, so that the both sides of the stand lever 36 can be supported rotatably in the lower space 56. The end portion of the stand lever 36 on the pin-like protrusions 37 side engages with the free end of a plate spring 38 one end of which is fixed to the bottom portions 22 by stop pins 57, and the end portion is normally held in the storage position shown in FIG. 3. Gutter grooves 39 to which the back portion 2 of the clip 1 is inserted movably are formed in the upper surfaces of the respective bottom portions 22, as shown in FIG. 5. Recess portions 40 which are a degree deeper are formed in the gutter grooves 39 on their front end side, so that the lower-side abutment portion 3 and a portion of the back portion 4 following the lower-side abutment portion 3 of the frontmost clip 1 should fall into this recess portions 40.

The handle portion 12 is constituted mainly by a handle cover 41 formed from synthetic resin, and a handle body 42 formed from synthetic resin or a metal plate. The handle cover 41 is formed so that an upper portion 43, opposite side portions 44, a front portion 45 and a rear portion 46 are formed integrally with each other to cover the handle body 42 from above, while the lower side is opened. On the other hand, the handle body 42 is formed like an approximately rectangular gutter having an upper portion 47 and opposite side portions 48, as shown in detail in FIG. 10. In each of the opposite side portions 48, a long hole 49 extending in the front/rear or longitudinal direction is formed on the rear end side, and two shaft holes 51 and 52 are formed at a distance in the front/rear or longitudinal direction on the front end side. A support shaft 53 is inserted through the opposite side portions 21 at their rear side of the driver body 11 and fitted loosely into the long holes 49. Accordingly, the handle portion 12 is supported so that it is movable forward by the longitudinal length of the long holes 49, and so that its forward side can rotate about the support shaft 53 as a fulcrum. A thumb-driven protrusion 50 on which a thumb can be placed is formed integrally on the front end of the upper portion 43 of the handle cover 41. At least the upper portion 43 of the handle cover 41 is formed from transparent synthetic resin. If band-like paper 6 on which a company name, a trade name, etc. have been printed is disposed between the upper portion 43 of the handle cover 41 and the upper portion 47 of the handle body 42 as indicated by a two-dotted chain line in FIG. 3, the printed surface of the paper 6 can be seen through the transparent upper portion 47. In this case, this clip driver 1 can be used as a souvenir for advertising the company or trade name.

The link portion 13 is provided so as to support front end portion of the handle portion 12 on the driver body so that the front end of the handle portion 12 moves forward down, and at the same time so as to support the slide member 14 so that the slide member 14 pushes the clip 1 to the position where sheets of paper will be clipped. The link portion 13 has a pair of first link bars 63 and a second link bar 65. The first link bars 63 are pivotally supported at their one ends on pin-like protrusions 61 outward projecting from the opposite side portions 21 of the driver body portions 11 respectively, and the second link bar 65 is pivotally supported at its one end by a support shaft 64 fitted at its opposite end portions into the shaft holes 52 of the handle body 42 respectively. The other ends of the first link bars 63 are supported pivotally on the opposite end portions of a support shaft 62 fitted at its opposite ends into the shaft holes 51 of the handle body 42, respectively. The other end of the second link bar 65 is connected to the slide portion 12 which will be described later.

The pair of first link bars 63 are constituted by flat metal plates respectively, and their other ends are disposed in the inside of the opposite side portions 48 of the handle body 42 respectively. In the other ends of these first link bars 63, long holes 66' are formed so as to extend in the longitudinal direction of these first link bars 63, and the support shaft 62 is inserted through these long holes 66'.

As shown in detail in FIG. 11, the second link bar 65 is shaped approximately into a gutter; for example, by pressing a metal plate so as to have opposite sides 66 and a bottom 67. Shaft holes 68 are made in the opposite ends of each of the opposite sides 66, and a lock hole 69 is made at one end of the bottom 67. The support shaft 64 is inserted through the shaft holes 68 on the one end side of the second link bar 65. In such a manner, the second link bar 65 is disposed between the pair of first link bars 63 so as to cross the latter.

The slide member 14 has a slide body 71 and a spring member 72. The slide body 71 is formed from synthetic resin or the like and slidably inserted into the open portion between the rear end of the front end upper cover portion 23 and the front end of the ceiling portion 24 of the driver body 10. The spring member 72 is constituted by a coil spring or the like so as to always pull the slide body 71 backward elastically and so as to give an elastic force to the handle portion 12 to always move up the front end side of the handle portion 12.

The slide body 71 is constituted by a push-out portion 73 which comes into contact with the back portion 2 of the clip 1 to thereby push out the clip 1, front protrusions 74 projecting substantially horizontally from the opposite side portions near the push-out portion 73 respectively for preventing the push-out portion 73 from moving up, a pair of shaft support protrusions 75 formed near the push-out portion 73 so as to project upward from the open portion of the driver body 10, and so as to be disposed at a distance in the direction perpendicular to the longitudinal or front/rear direction, and rear protrusions 76 projecting substantially horizontally from the opposite sides of the end portion opposite to the push-out portion 73 so as to prevent the rear end portion of the slide body 71 from moving up, as shown in FIG. 3. The respective upper surfaces of the front protrusions 74 and the rear protrusions 76 engage with the lower surface of the protrusions 27 of the inner surfaces of the side portions 21 of the driver body 10 when the slide body 71 moves up to thereby prevent the slide body 71 from moving up more. In addition, in order to make it sure to insert the apexes of the pair of clip opening springs 15 into the guide portions 5 of the clip 1 when the clip 1 is pushed out, a pent-roof portion 77 for stopping the corner between the back portion 2 and the upper abutment portion 3 of the clip 1 is formed integrally with the upper end of the push-out portion 73. A rear end surface 78 of the slide body 71 is made to form a slope which inclines toward the front end.

A support shaft 79 is inserted through the pair of shaft support protrusions 75 so as to be supported thereby substantially horizontally. The support shaft 79 is loosely inserted through the shaft hole 68 formed on the other end side of the second link bar 65. Further, a slope 80 inclined obliquely upward toward the rear end is formed on the lower surface on the push-out portion 73 side. In the side between the lower front protrusions 74 and the rear protrusions 76 of the slide body 71 and above these protrusions 74 and 76, a restriction protrusion 81 is formed so as to project substantially horizontally. When the slide body 71 is moved down, the lower surface of the restriction protrusion 81 engages with the upper surface of the protrusions 27 of the driver body 10 so as to prevent the slide body 71 from further moving down. In addition, a stopper step portion 84 which contacts with the rear edge of the front end upper cover portion 23 when the slide body 71 is moved forward is formed at the boundary portion between the push-out portion 73 and the shaft support protrusion 75.

One end of the spring member 72 is locked in the lock hole 69 of the second link bar 65, while the other end is locked on the support shaft 53 supporting the rear portion of the handle portion 12. This spring member 72 gives the second link bar 65 an urging force to rotate the lower end side of the second link bar 65 anticlockwise in FIG. 3 with the support shaft 64 as a fulcrum, so that the front end of the handle portion 12 is always moved up. On the other hand, the rear end surface 78 of the slide member 14 is brought into contact with the front end surface of the ceiling portion 24 by the spring member 72 to incline the push-out portion 73 so as to move up. The moving-up of the push-out portion 73 is restricted when the front protrusions 74 engage with the lower surfaces of the protrusions 27 of the driver body 10.

The longitudinal or front/rear direction of the slide body 71 or the length of the ceiling portion 24 is set so that the push-out portion 73 of the slide body 71 is located at the rear of the first or frontmost clip 1 and above the abutment portions 3 6f the second clip 1 when the handle portion 12 moves up and the rear end surface 78 of the slide body 71 contacts with the front end of the ceiling portion 24 as shown in FIG. 3. In addition, step portions 82 extending near the lower end portions of the first link bars 63 and horizontally in the front/rear direction are formed in the outer surfaces of the side portions 21 of the driver body 10, so that the first link bars 63 do not project from the outer surfaces of the side portions 21. In addition, portions 83 of the side portions 21 near the first link bars 63 are extended upward longer than any other portion, so that the support shaft 61 is reinforced, and the handle portion 12 and the first and second link bars 63 and 65 are prevented from twisting or rolling.

Figure 12:
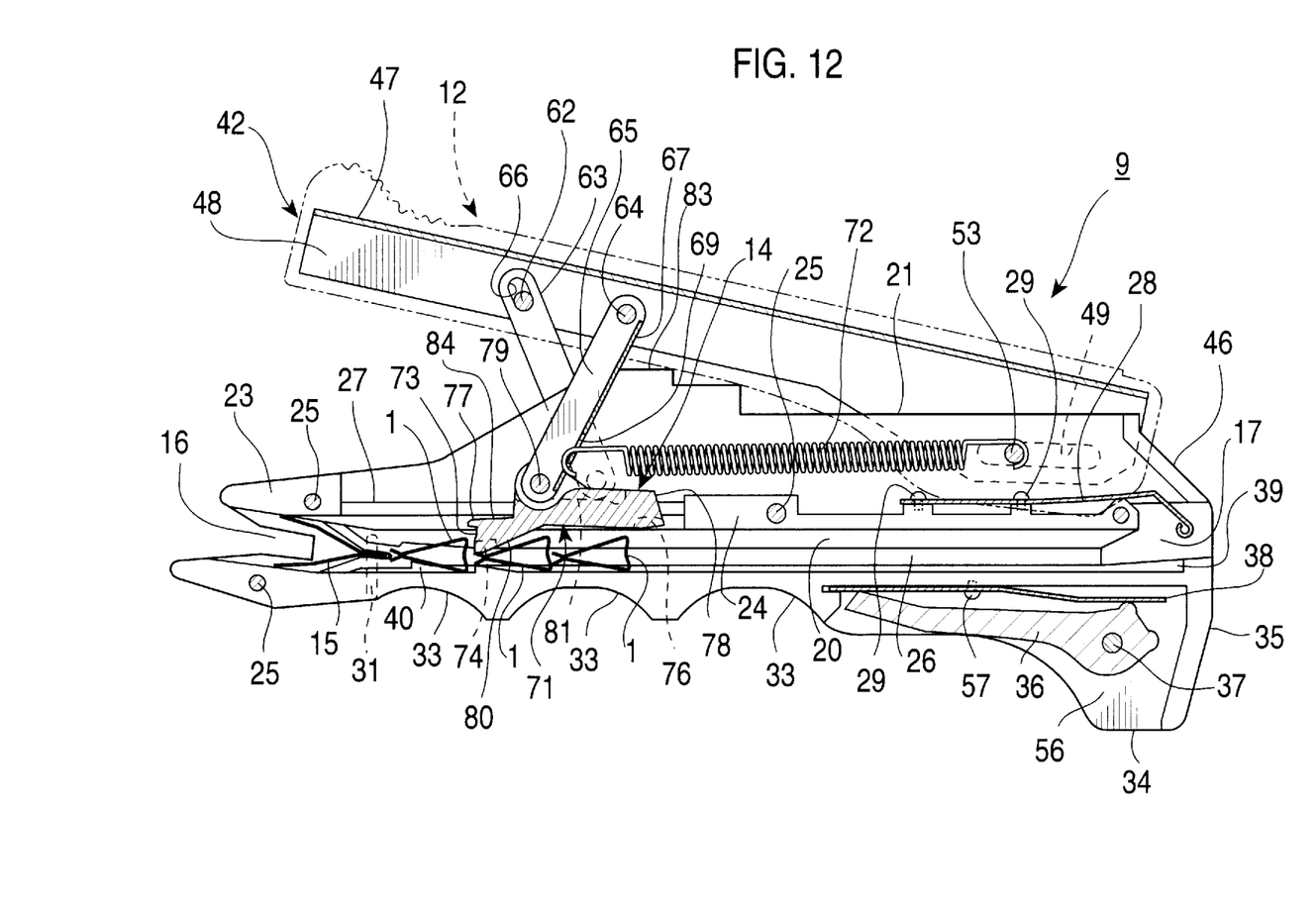
FIG. 12 is a vertically sectioned side view for explaining the state of the embodiment in which a first clip is being pushed forward.
Figure 13:
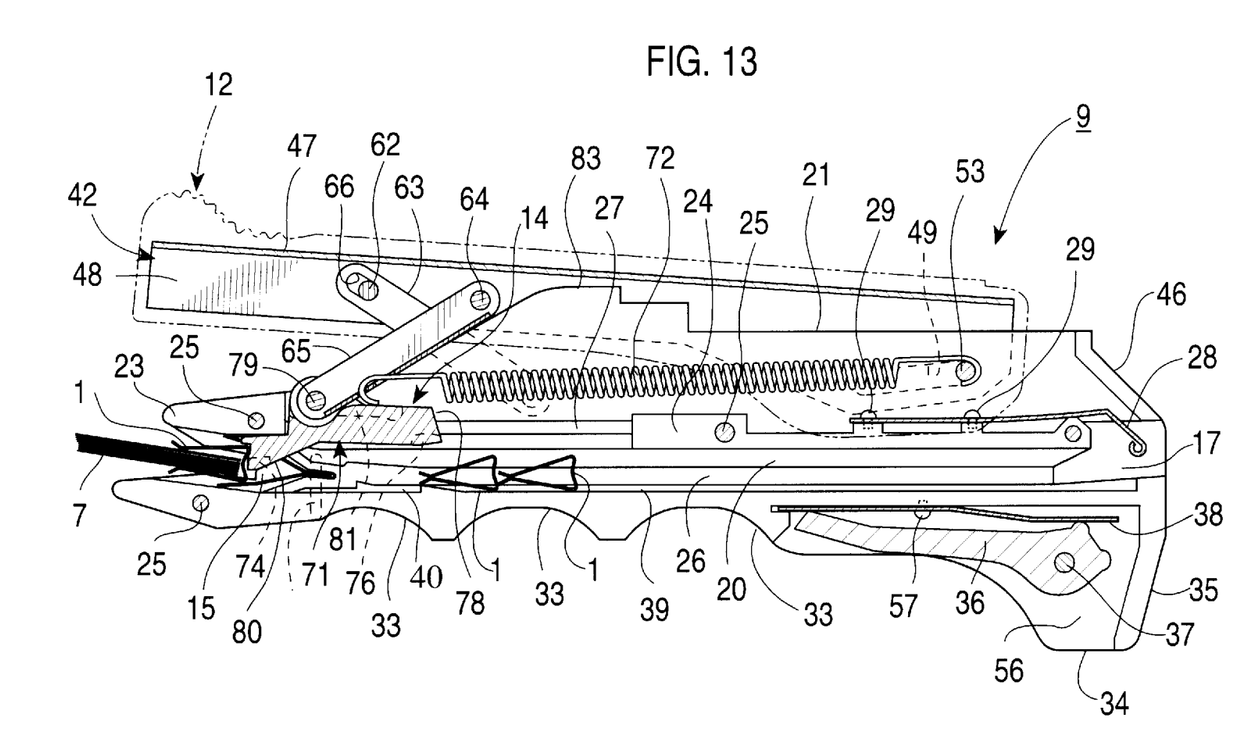
FIG. 13 is a vertically sectioned side view for explaining the state of the embodiment in which a clip holding sheets of paper in it can be taken out.

Next, the manner of use and operation of the thus configured clip driver 9 will be described with reference to FIG. 3 and FIGS. 12 and 13. FIG. 12 is a vertically sectioned side view for explaining the state in which the first clip is pushed out, and FIG. 13 is a vertically sectioned side view for explaining the state in which the clip holding sheets of paper in it can be taken out.

First, a plurality of clips 1 are charged one by one into the clip driver 9. When charged, each clip 1 is inserted into the clip insertion inlet 17 from the guide portions 5 of the clip 1 while the paper insertion inlet 16 is put down. Although the clip insertion inlet 17 is partly covered with the insertion inlet cover 28, if the clip 1 is pushed from its guide portions 5 into the open portion of the clip insertion inlet 17 which is not covered with the edge of the insertion inlet cover 28, as shown in FIG. 3, the clip 1 can be charged easily. This is because the slope of the upper abutment portion 3 of the clip 1 pushes up the edge of the insertion inlet cover 28. The clips 1 charged into the clip driver 9 are prevented from coming off by means of the insertion inlet cover 28 even if the clip insertion inlet 17 side of the clip driver 9 is put down.

The clips 1 charged from the clip insertion inlet 17 in such a manner as mentioned above are sent forward one by one while the lug portions 4 on the opposite sides of each clip 1 enter the lug guide grooves 26 of the driver body 10 and the abutment portions 3 of each clip 1 enter the clip guide grooves 20. When the paper insertion inlet 16 side is put down, the first clip 1 falls into the recess portion 40 formed in the front end of the gutter-like groove 39 of the bottom portion 22 of the driver body 10 so as to be disposed in a degree lower position, as shown in FIG. 3. At this time, the apexes of the clip opening springs 15 are disposed between the guide portions 5 of the lug portions 4 of the first clip 1. After the first clip 1 falls into the recess portion 40, there is no fear that the first clip 1 slides and falls toward the clip insertion inlet 17 from the recess portion 40, even if the clip insertion inlet 17 side of the clip driver 9 is put down to some extent.

In this state, though not shown in FIG. 3, edge portions of sheets of paper to be clipped are inserted into the paper insertion inlet 16. Next, the clip driver 9 is gripped by hand while the first, second and third fingers are placed on the three recess portions 33 formed in the bottom portion 22, and the top end of the thumb is put on the thumb-driven protrusion 50 of the upper portion 43 of the handle cover 41 with the thenar eminence put on the upper portion 43. Consequently, first, a moving-down force is given to the handle portion 12, so that the support shaft 62 moves down by a distance corresponding to the clearance of the long holes 66' of the first link bars 63, so that, at first, through the handle portion 12 and the second link bar 65, the front end of the slide portion 14 moves down substantially vertically by a distance corresponding to the clearance of the long holes 66'.

When the gripping force is further increased, the handle portion 12 rotates while moving forward along the long hole 49 of the handle body 42 against the bias force of the spring member 72 because the support shaft 53 which is a rotation fulcrum of the handle portion 12 is pivotally supported in the long hole 49. Because of the rotation and advance down of the handle portion 12, the second link bar 65 makes the push-out portion 73 of the slide portion 14 descend into the driver body 10, as shown in FIG. 12. The descent of the push-out portion 73 is inhibited when the restriction protrusion 81 of the slide portion 14 engages with the protrusions 27 of the driver body 10. At this time, the push-out portion 73 is located at the rear of the first clip 1 and above the abutment portions 3 of the next clip 1, as shown in FIG. 13. As mentioned above, since the lower surface of the slide body 71 on the push-out portion 73 side is made to be the slope 80 which is inclined obliquely upward toward the rear end, there is no case where the descent of the push-out portion 73 is inhibited by the next clip 1.

When the driver body 10 and the handle portion 12 are gripped further, the first link bars 63 rotates anticlockwise in FIG. 12 around the pin-like protrusion 61 as a fulcrum. Accordingly, the handle portion 12 further moves forward along the long hole 49. On the other hand, the second link bar 65 rotates clockwise in FIG. 12 around the support shaft 64 as a fulcrum, so that the slide body 71 connected to the lower end of the second link bar 65 is further moved forward along the protrusion 27. At this time, because the handle portion 12 is also advanced as mentioned above, the slide body 71 can be advanced with a larger stroke than the amount of advance caused only by the rotation of the second link bar 65. Accordingly, the push-out portion 73 of the slide portion 14 contacts with the back portion 2 of the first clip 1, so that the first clip 1 is moved forward and forward. At this time, the pent-roof portion 77 formed at the upper end of the push-out portion 73 presses the upper corner between the back portion 2 and the upper abutment portion 3 of the clip 1, the first clip 1 can be advanced surely. The first clip 1 which have moved forward holds the apexes of the clip opening springs 15 between the guide portions 5 of the opposite lug portions 4. When the clip 1 is further moved forward, its guide portions 5 of the opposite lug portions 4 are sent to the opened free ends of the clip opening springs 15 respectively. The first clip 1 are sent to the paper insertion inlet 16 in a state where the nip between the opposite lug portions 4, that is, the abutment portions 3 is opened by the opened free ends of the pair of clip opening springs 15. Since the sheets of paper 7 (see FIG. 13) are inserted into the paper insertion inlet 16, the sheets of paper 7 are held between the opened abutment portions 3.

When the driver body 10 and the handle portion 12 are further gripped, the first link bars 63 rotates anticlockwise to thereby move the handle portion 12 further forward, while the second link bar 65 rotates clockwise to thereby move the slide body 71 further forward along the protrusions 27. Accordingly, the lug portions 4 of the first clip 1 is released from the engagement with the clip opening springs 15, so that the first clip 1 holding the sheets of paper 7 is removed from the free ends of the clip opening springs 15. The clip 1 released from the force of the clip opening springs 15 for opening the abutment portions 3 is discharged from the paper insertion inlet 16 while holding the sheets of paper firmly between the abutment portions 3 by the elasticity thereof, as shown in FIG. 13. The rotation of the handle portion 12 is restricted by the fact that the stopper step portion 84 formed in the boundary portion between the push-out portion 73 of the slide body 71 and the shaft support protrusions 75 abuts against the rear edge of the front end upper cover portion 23. On the other hand, the advance of the handle portion 12 is restricted by the fact that the support shaft 53 is located at the rear end of the long hole 49 of the handle body 42.

If the pressing force given to the handle portion 12 by the thumb and the thenar eminence is loosened at the time when the engagement between the lug portions 4 of the clip 1 and the clip opening springs 15 has been released, the lower end of the second link bar 65 is brought back toward the rear end by the spring member 72, so that the second link bar 65 stands up while rotating anticlockwise around the support shaft 64 as a fulcrum. With this, the slide body 71 also moves back, and the first link bars 63 also stands up while rotating clockwise around the pin-like protrusions 61 as a fulcrum, so that the handle portion 12 returns to its initial position. The return of the handle portion 12 to the initial position is terminated when the front protrusions 74 of the slide body 71 engage with the lower surfaces of the protrusions 27, and the support shaft 53 is located at the front end of the long hole 49 of the handle body 42. Although the slide body 71 also moves back at that time, the push-out portion 73 at the front end of the slide body 71 is put up by the spring member 72 when the pressing force given to the handle portion 12 is loosened. Accordingly, since the front end portion of the slope 80 does not project into the clip guide groove 20, there is no case where the next clip 1 is returned to the clip insertion inlet 17 from the slide body 71, or the next clip 1 prevents the slide body 71 from returning to the initial position.

Figure 14:
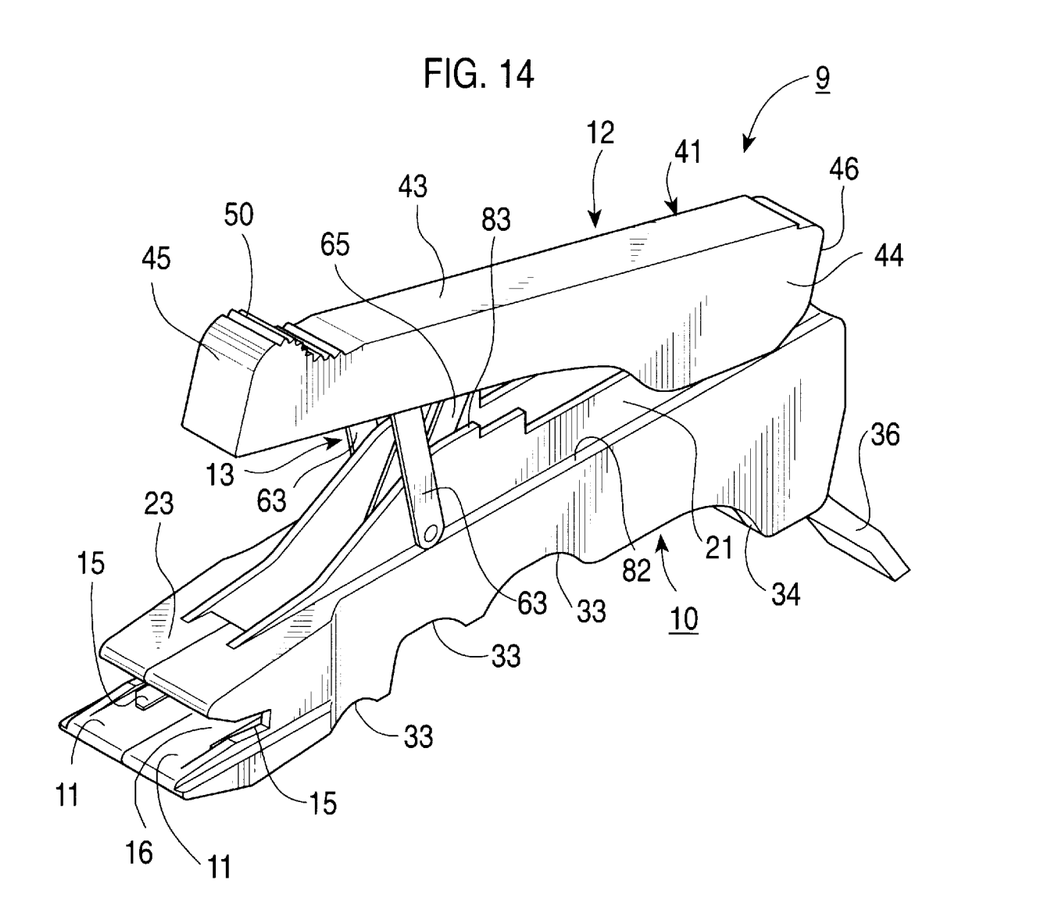
FIG. 14 is a perspective view illustrating the embodiment in which an auxiliary foot has been set up.

When the clip driver 9 is to be used on a desk, it will do to rotate the free end side of the stand lever 36 stored in the lower space 56 on the rear end side of the bottom portions 22 of the driver body 10 to set up as shown in FIG. 14. Accordingly, the paper insertion inlet 16 side of the clip driver 9 is put down, while the clip insertion inlet 17 side thereof is put up, so that the clips 1 slide and fall in the clip guide grooves 20 due to their own weight and they can be fed to the recess portion 40 sequentially. At the end portion of this stand lever 36 on the pin-like protrusion 37 side, a surface parallel to the plate spring 38 is formed so as to be pressed elastically by the plate spring 38 to thereby keep the state of the stand lever 36 when the stand lever 36 is set up. It is therefore possible to keep the stand lever 36 in the standing state surely.

As is apparent from the above description, according to the first aspect of the present invention, the clip driver is provided with a handle means one end of which is pivotally supported on the rear end side of the driver body rotatably and movably in the front/rear direction while the other end of which is disposed on the front end side of the driver body, and a connection means for connecting the driver body, the slide means and the handle means to each other so as to move the slide means in the front/rear direction in response to the rotation and movement of the handle means to thereby feed the clip to the paper insertion inlet over the clip opening springs. Accordingly, sheets of paper can be clipped by the clip surely by such a simple operation that the handle means is merely gripped so that the handle means is pressed toward the driver body. It is therefore possible for anyone to clip sheets of paper very easily.

According to the second aspect of the present invention, in the above clip driver, a front-end upper portion of the clip path in the driver body is open to form an opening, and the slide means is disposed movably in the front/rear direction so as to close the opening partially. Accordingly, it is possible to feed a clip from the clip opening springs to the paper insertion inlet with a simple configuration.

According to the third aspect of the present invention, in the above clip driver, the slide means is always urged merely elastically toward the rear end by an elastic member. Accordingly, an enough force to move the slide means forward against the elasticity of the elastic member is obtained by such an easy operation that one end of the handle means is rotated and moved forward. Therefore, the slide means can return by such an operation that the pressure to the handle means is merely released by the elastic force of the elastic member.

According to the fourth aspect of the present invention, in the above clip driver, the support shaft of the driver body can move in long holes of the handle body. By this very simple structure, it is possible to move the handle means in the front/rear direction surely.

According to the fifth aspect of the present invention, in the above clip driver, the connection means can be constituted by a light and simple structure which has a first connection member for supporting the handle means rotatably on the driver body, and a second connection member for moving the slide means in the front/rear direction by the rotation of the handle means.

According to the sixth aspect of the present invention, the above clip driver has a very simple configuration in which the first connection means is constituted by a pair of link bars disposed so as to sandwich the opposite sides of the driver body, and the second connection member is constituted by one link bar disposed rotatably between the opposite sides of the driver body. Accordingly, it is possible to provide a clip driver which can be reduced in weight.

According to the seventh aspect of the present invention, in the above clip driver, the handle means can move forward surely by a distance corresponding to the longitudinal length of the long holes of the handle body, and the slide means is connected to one connection member of the connection means. Accordingly, the slide means can move forward surely with the handle means rotating and moving forward. In addition, only by releasing the pressure to the handle means, the slide means can be returned together with the connection means by the elastic member.

According to the eighth aspect of the present invention, in the above clip driver, at least the upper surface of a handle cover is made to be transparent. Accordingly, by applying different colors to the driver body and the handle body which are separate members from each other, or by printing a trade name, a company name, or an official notice on the upper surface of the handle body, it is possible to provide a clip driver which can be colored with a number of colors or which can appeal the trade name or the company name.

According to the ninth aspect of the present invention, in the above clip driver, by such a simple operation that a print medium is put on the upper surface of the handle body, it is possible to provide a clip driver which can appeal a trade name or a company name. Since the print medium may be paper, it is possible to put the clip driver into practice at a very low price.

According to the tenth aspect of the present invention, in the above clip driver, a stand lever may be set up in the case where the clip driver is used on a desk. Accordingly, clips slide and fall inside the driver body because of their own weight so that they can be fed toward the paper insertion inlet sequentially.

What is claimed is:

1. A clip driver for driving clips each of which is formed from an elastic plate-like body so as to be constituted by a back portion, and abutment portions formed by bending said elastic plate-like body in the same direction at opposite ends of said back portion so that opposite ends of said abutment portions abut against each other elastically whereby the clip can hold edge portions of sheet-like members to be clipped between said opposite ends of said abutment portions, comprising:

a driver body for accommodating a plurality of said clips, said driver body including a paper insertion inlet formed at a front end for inserting said sheet-like members to be clipped, a clip insertion hole formed at a rear end for inserting said clips one by one, and a clip path formed to extend from said paper insertion inlet to said clip insertion inlet;

a pair of clip opening springs disposed on said driver body near said paper insertion inlet for opening a nip between said abutment portions of said clip in the opposite directions;

a slide means disposed in said driver body on said front end side so as to be movable in a front/rear direction for feeding a frontmost one of said clips in said clip path toward said paper insertion inlet over said clip opening springs by means of a front end of said slide means;

a handle means one end of which is pivotally supported on said rear end side of said driver body rotatably and movably in the front/rear direction while the other end of which is disposed on said front end side of said driver body; and a connection means for connecting said driver body, said slide means and said handle means to each other so as to move said slide means in the front/rear direction in response to the rotation and movement of said handle means to thereby feed said clip to said paper insertion inlet over said clip opening springs.

2. A clip driver according to claim 1, wherein a front-end upper portion of said clip path in said driver body is open to form an opening, and said slide means is disposed movably in the front/rear direction so as to close said opening partially.

3. A clip driver according to claim 1, wherein said slide means has an elastic member for enabling said slide means to move forward when one end of said handle means moves forward while rotating, and for making said slide means move backward by an elastic force of said elastic member when said handle means returns.

4. A clip driver according to claim 1,
wherein said driver body has a pair of side wall portions provided so as to stand at a distance in a direction perpendicular to said front/rear direction, and a support shaft provided across said side wall portions perpendicularly thereto on said rear end side of said driver body; and
wherein said handle means includes a handle body having long holes formed in a rear end portion of said handle body so as to extend in the front/rear direction so that said support shaft is inserted rotatably in said long hole.

5. A clip driver according to claim 1, wherein said connection means has a first connection member one end of which is connected to said driver body and the other end of which is connected to said handle means rotatably, and a second connection member one end of which is connected to said handle means and the other end of which is connected to said slide means rotatably, said first and second connection members moving said handle means and said slide means in the front/rear direction respectively by pressing said handle means.

6. A clip driver according to claim 5, wherein said first connection means is constituted by a pair of link bars disposed to sandwich opposite sides of said driver body, while said second connection member is constituted by a single link bar disposed to rotate between said opposite sides of said driver body.

7. A clip driver according to claim 1,
wherein said driver body includes a pair of side wall portions provided to stand at a distance in a direction perpendicular to the front/rear direction of said driver body, and a support shaft provided across said side wall portions so as to extend perpendicularly to said side wall portions on the rear end side of said driver body;
wherein said handle means includes a handle body having a long hole extending in the front/rear direction so that said support shaft is inserted rotatably in said long hole at a rear end portion of said handle body;
wherein said connection means has a first connection member one end of which is connected to said driver body and the other end of which is connected to said handle means rotatably, and a second connection member one end of which is connected to said handle means and the other end of which is connected to said slide means rotatably; and
wherein said slide means has an elastic member one end of which is connected to said support shaft and the other end of which is connected to said slide means for enabling said slide means to move forward when one end of said handle means moves forward while rotating, and for making said slide means move backward by an elastic force of said elastic member when said handle means returns.

8. A clip driver according to claim 1, wherein said handle means includes a handle body one end of which is pivotally supported on the rear end side of said driver body so as to be rotatable and movable in the front/rear direction, a handle cover which is formed to cover said handle body and at least an upper surface of which is transparent to be able to see an upper surface of said handle body through said upper surface of said handle cover.

9. A clip driver according to claim 1, wherein a print medium on which a company name, a trade name, an official notice, etc. are printed is put on the upper surface of said handle body.

10. A clip driver according to claim 1, wherein a lower space is provided in a bottom portion on the rear end side of said driver body, said lower space accommodating a stand lever for positioning said driver body obliquely so that said paper insertion inlet side is put down while said clip insertion inlet side is put up when said stand lever is set up.

* * * * *